United States Patent
Neikirk et al.

(10) Patent No.: US 9,581,559 B2
(45) Date of Patent: Feb. 28, 2017

(54) CORROSION DETECTION SENSOR EMBEDDED WITHIN A CONCRETE STRUCTURE WITH A DIFFUSION LAYER PLACED OVER THE SACRIFICIAL TRANSDUCER

(71) Applicant: Board of Regents, The University of Texas System, Austin, TX (US)

(72) Inventors: Dean P. Neikirk, Austin, TX (US); Sharon L. Wood, Austin, TX (US); Praveenkumar Pasupathy, Austin, TX (US); Ali Abu Yosef, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 282 days.

(21) Appl. No.: 14/459,474

(22) Filed: Aug. 14, 2014

(65) Prior Publication Data
US 2015/0048844 A1  Feb. 19, 2015

Related U.S. Application Data

(60) Provisional application No. 61/867,448, filed on Aug. 19, 2013.

(51) Int. Cl.
*G01N 27/02* (2006.01)
*G01N 17/04* (2006.01)
*G01N 33/38* (2006.01)

(52) U.S. Cl.
CPC .......... *G01N 27/021* (2013.01); *G01N 17/04* (2013.01); *G01N 33/383* (2013.01)

(58) Field of Classification Search
CPC .... G01N 27/021; G01N 27/026; G01N 27/26; G01N 17/00; G01N 17/02; G01N 17/04; G01N 33/383
See application file for complete search history.

(56) References Cited

U.S. PATENT DOCUMENTS 5,744,794 A * 4/1998 Michie .................. G01M 3/047
250/227.16
2002/0166996 A1  11/2002 Malric et al.
(Continued)

OTHER PUBLICATIONS

P. Pasupathy, A. Abu Yousef, D. P. Neikirk, and S. L. Wood; "Wireless Electronic Structural Surveillance Sensors Using Inductively Coupled Sacrificial Transducers"; Piers Online, vol. 7, No. 6, 2011; pp. 511-515.*

(Continued)

*Primary Examiner* — Son Le
(74) *Attorney, Agent, or Firm* — Robert A. Voight, Jr.; Winstead, P.C.

(57) ABSTRACT

A corrosion detection sensor embedded within a concrete structure. The sensor includes a hermetically sealed resonant circuit that is a resistor-inductor-capacitor (RLC) circuit. The sensor further includes a sacrificial transducer that is inductively or capacitively coupled to the resonant circuit, where the sacrificial transducer is exposed to an environment outside the sensor to monitor corrosion of steel reinforcement in the concrete structure. Additionally, the sensor includes a protective cementitious housing surrounding the resonant circuit and the sacrificial transducer. The sensor further includes a diffusion layer placed over the sacrificial transducer, where the diffusion layer enables a dispersion of a chemical species over the sacrificial transducer. In this manner, a more uniform distribution of the chemical species over the surface of the sacrificial transducer mitigating the localized corrosion is ensured. Furthermore, such a design is less susceptible to false positives.

25 Claims, 1 Drawing Sheet

(56) References Cited

U.S. PATENT DOCUMENTS

| | | |
|---|---|---|
| 2003/0075457 A1 | 4/2003 | Buenfeld et al. |
| 2003/0101898 A1 | 6/2003 | Standke et al. |
| 2008/0136425 A1* | 6/2008 | Holst .................... G01N 17/04 |
| | | 324/691 |
| 2009/0218545 A1 | 9/2009 | Mader et al. |
| 2010/0108510 A1 | 5/2010 | Hill |
| 2013/0269283 A1 | 10/2013 | Hussain et al. |

OTHER PUBLICATIONS

Pasupathy et al., "Versatile Wireless Sacrificial Transducers for Electronic Structural Surveillance Sensors," Sensors, 2009 IEEE, Oct. 25-28, 2009, pp. 1-5.

\* cited by examiner

CORROSION DETECTION SENSOR EMBEDDED WITHIN A CONCRETE STRUCTURE WITH A DIFFUSION LAYER PLACED OVER THE SACRIFICIAL TRANSDUCER

CROSS REFERENCE TO RELATED APPLICATIONS

This application is related to the following commonly owned U.S. Patent Application:

Provisional Application Ser. No. 61/867,448, "Diffusion Layer Enhanced Passive Wireless Sensor with Wireless Transduction," filed Aug. 19, 2013, and claims the benefit of its earlier filing date under 35 U.S.C. §119(e).

GOVERNMENT INTERESTS

The U.S. Government has certain rights in this invention pursuant to the terms of the National Institute of Standards and Technology—Technology Innovation Program (NIST-TIP) Grant No. 70NANB9H9011.

TECHNICAL FIELD

The present invention relates generally to monitoring corrosion in steel reinforcement in concrete structures, and more particularly to a corrosion detection sensor embedded within a concrete structure with a diffusion layer placed over the sacrificial transducer.

BACKGROUND

Structural degradation of concrete structures due to corrosion of the reinforcing steel is one of the most extensive durability problems facing concrete structures. This gives rise to concerns about structural safety, integrity, and serviceability. As a result, monitoring the corrosion of the steel reinforcement in the concrete structures is greatly desired so as to detect the state of corrosion of the reinforcing steel in these concrete structures thereby being able to address the corrosion through preventive remedial measures and economic repairs before it leads to severe structural damage or failure. By being able to implement preventive remedial measures prior to severe structural damage or failure, the overall life-cycle costs in maintaining and repairing the concrete structures will be lower than the cost of rehabilitating such structures after the point of severe structural damage or failure.

Monitoring this corrosion is difficult though since the embedded steel is not visible to the naked eye. Furthermore, detection techniques are needed to indicate initiation of corrosion so that remedial action can be taken before the damage is irreversible. Detection techniques, such as acoustic, ultrasonic and radar, have proved to be limited in this capacity.

Conventional corrosion monitoring techniques, such as half-cell potential and linear polarization, provide instantaneous measurements which are highly subject to the conditions (e.g., moisture, temperature) during measurement. Alternatively, sensors that are placed within the concrete structures using a sacrificial corroding element provide the most direct measurement of corrosion. However, obtaining this data requires electrical access, such as by wire, to the sensor. Any methods that require running wires breach the concrete and provide an ingress point for corrosive agents.

As a result, monitoring the corrosion of the steel reinforcement in concrete structures without breaching the concrete, such as by running wires, would greatly advance the ease and accuracy in measuring the corrosion. Furthermore, given the need for long-term monitoring of these concrete structures, such monitoring devices should be battery-free, cost effective, durable and reliable.

BRIEF SUMMARY

In one embodiment of the present invention, a corrosion detection sensor embedded within a concrete structure comprises a hermetically sealed resonant circuit comprising an inductor, a resistor and a capacitor. The corrosion detection sensor further comprises a sacrificial transducer that is inductively or capacitively coupled to the resonant circuit, where the sacrificial transducer is exposed to an environment outside the sensor to monitor corrosion of steel reinforcement in the concrete structure. The corrosion detection sensor additionally comprises a protective cementitious housing surrounding the resonant circuit and the sacrificial transducer. Furthermore, the corrosion detection sensor comprises a diffusion layer placed over the sacrificial transducer, where the diffusion layer enables a dispersion of a chemical species over the sacrificial transducer.

In another embodiment of the present invention, an electronic structural surveillance system comprises a corrosion detection sensor embedded within a concrete structure. The sensor comprises a hermetically sealed resonant circuit comprising an inductor, a resistor and a capacitor. The sensor further comprises a sacrificial transducer that is inductively or capacitively coupled to the resonant circuit, where the sacrificial transducer is exposed to an environment outside the sensor to monitor corrosion of steel reinforcement in the concrete structure. The sensor additionally comprises a protective cementitious housing surrounding the resonant circuit and the sacrificial transducer. Furthermore, the sensor comprises a diffusion layer placed over the sacrificial transducer, where the diffusion layer enables a dispersion of a chemical species over the sacrificial transducer. The surveillance system additionally comprises an external reader configured to interrogate the sensor by using magnetic coupling between a coil of the reader and the resonant circuit.

In another embodiment of the present invention, a corrosion detection sensor embedded within a concrete structure comprises a hermetically sealed resonant circuit comprising an inductor, a resistor and a capacitor. The corrosion detection sensor further comprises a plurality of sacrificial transducers that are inductively or capacitively coupled to the resonant circuit, where the plurality of sacrificial transducers are exposed to an environment outside the sensor to monitor corrosion of steel reinforcement in the concrete structure. The corrosion detection sensor additionally comprises a protective cementitious housing surrounding the resonant circuit and the plurality of sacrificial transducers. In addition, the corrosion detection sensor comprises one or more diffusion layers placed over one or more of the plurality of sacrificial transducers, where the one or more diffusion layers enable a dispersion of a chemical species over the one or more of the plurality of sacrificial transducers.

In another embodiment of the present invention, a corrosion detection sensor embedded within a concrete structure comprises a hermetically sealed RFID tag. The corrosion detection sensor comprises a sacrificial transducer that is inductively or capacitively coupled to the RFID tag, where the sacrificial transducer is exposed to an environment outside the sensor to monitor corrosion of steel reinforcement in the concrete structure. The corrosion detection sensor further comprises a protective cementitious housing surrounding the RFID tag and the sacrificial transducer. Furthermore, the corrosion detection sensor comprises a diffusion layer placed over the sacrificial transducer, where the diffusion layer enables a dispersion of a chemical species over the sacrificial transducer.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE SEVERAL VIEWS OF THE DRAWINGS

A better understanding of the present invention can be obtained when the following detailed description is considered in conjunction with the following drawings, in which.

DETAILED DESCRIPTION

While the following discusses the present invention in connection with measuring the corrosion of steel reinforcement in concrete structures, the principles of the present invention may be applied to other environments, such as chemical and biomedical, where the concept of using a diffusion membrane to ensure the uniform dispersion of a chemical species of interest is desired. A person of ordinary skill in the art would be capable of applying the principles of the present invention to such implementations. Further, embodiments applying the principles of the present invention to such implementations would fall within the scope of the present invention.

Furthermore, while the following discusses the present invention in connection with using passive circuitry, the present invention may also utilize active circuitry. A person of ordinary skill in the art would be capable of applying the principles of the present invention to such implementations. Further, embodiments applying the principles of the present invention to such implementations would fall within the scope of the present invention.

The present invention presents a new class of passive wireless corrosion sensors. The noncontact (NC) sensor platform provides an economical and nondestructive means for detecting corrosion initiation within concrete. The sensor is powered through the inductive coupling to an external mobile reader that can be handheld or mounted on a vehicle. It is envisioned that the sensor will be embedded in concrete during construction and interrogated sporadically over the service life of the structure. The sensor output can be used to detect corrosion initiation within concrete and is expected to enhance the quality information collected during qualitative routine bridge inspections.

In one embodiment, the NC sensor prototype consists of a resonant circuit that is inductively coupled to a sacrificial transducer. Corrosion of the sacrificial element alters the measured sensor response and is used to detect corrosion within concrete. Unlike the traditional corrosion evaluation methods, such as half-cell potentials, the output of the sensors of the present invention is insensitive to environmental variations.

Figure 1:
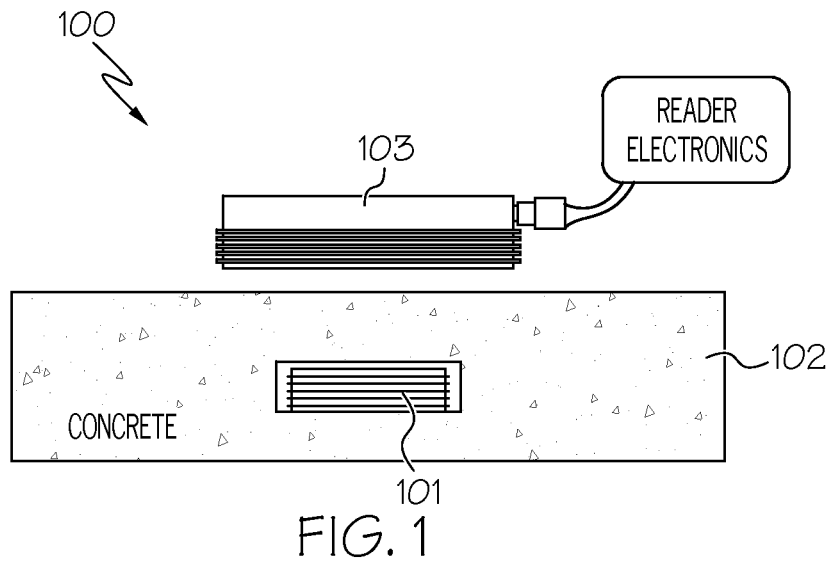
FIG. 1 illustrates a configuration of an electronic structural surveillance (ESS) system in accordance with an embodiment of the present invention.

Referring now to the Figures, FIG. 1 illustrates a configuration of an electronic structural surveillance (ESS) system 100 in accordance with an embodiment of the present invention. As illustrated in FIG. 1, ESS system 100 includes a passive (battery-less) wireless sensor 101 embedded within a concrete structure 102. In one embodiment, sensor 101 is hermetically sealed. In one embodiment, sensor 101 operates using magnetic coupling between an external reader coil 103 and sensor 101 (resonant circuit of sensor) enabling non-destructive long-term monitoring of civil infrastructure. Specifically, as discussed further herein, passive sensor 101 includes a transduction layer that supports non-contact interaction with the resonant sensor's circuitry. One application of ESS system 100 is in the detection of corrosion of embedded steel reinforcement in concrete structures 102. As discussed further herein, sensor 101 includes a sacrificial corroding transducer/element to monitor the corrosion. By allowing wire-free interaction between the exposed transducer and the hermetically sealed sensor circuitry, the transducer remains fully exposed to the environment that it is monitoring yet does not compromise the sensor electronics by breaching the hermetic seal. A more detail description of the design of the embedded passive wireless sensor 101 is provided below in connection with FIG. 2.

Figure 2:
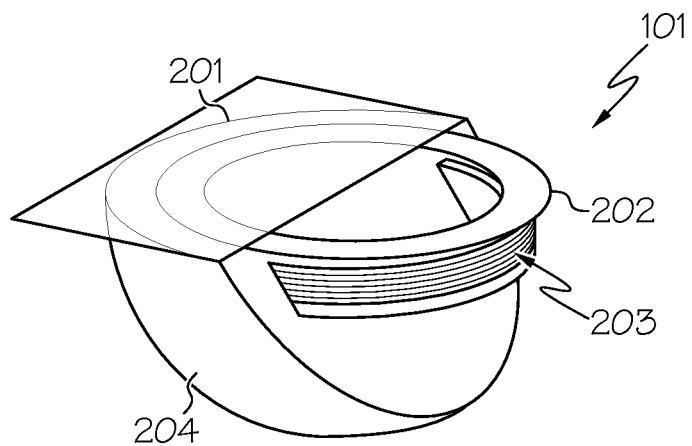
FIG. 2 illustrates a design of the corrosion detection sensor in accordance with an embodiment of the present invention.

FIG. 2 illustrates a design of the corrosion detection sensor 101 in accordance with an embodiment of the present invention. Referring to FIG. 2, in conjunction with FIG. 1, sensor 101 includes a diffusion layer 201 that is placed over a sacrificial layer 202. Diffusion layer 201 may be designed to be hydrophilic or hydrophobic and/or semi-permeable (chemical or physical specificity). Sacrificial layer 202 is a corroding transducer/element that is exposed to the environment so as to monitor the corrosion of the steel reinforcement in concrete structure 102. That is, sacrificial transducer 202 is subject to the same environmental conditions as the surrounding concrete. Corrosion of the sacrificial element 202 alters the measured sensor response and is used to detect corrosion within concrete. Furthermore, sacrificial transducer 202 is capable of non-contact (wire-free) interaction, through hermetically sealed packaging, with sensor electronics. While the following discusses transducer 202 as being sacrificial, the principles of the present invention are not to be limited as such and may utilize non-sacrificial type transducers 202. Furthermore, sacrificial transducer 202 can be resistive, capacitive or inductive. Additionally, while FIG. 2 illustrates a single transducer 202, sensor 101 may include multiple transducers 202, with/without a diffusion layer 201, thereby allowing a multi-threshold sensor (e.g., ternary or quaternary threshold corrosion sensor). Each of these diffusion layers 201 placed over a sacrificial transducer 202 enables a dispersion of a chemical species over those sacrificial transducers 202.

Sensor 101 further includes a hermetically sealed resonant circuit 203 that is inductively coupled to sacrificial transducer 202. Alternatively, transducer 202 may be capacitively coupled to resonant circuit 203. In one embodiment, resonant circuit 203 is a resistor-inductor-capacitor (RLC) circuit. While FIG. 2 illustrates sensor 101 including a resonant circuit 203, the principles of the present invention may include the use of RFID tags (RFID chip plus a resonant circuit) to replace resonant circuit 203. The placement of sacrificial transducer 202 in the vicinity of an RFID tag should induce similar inductive effects as with resonant circuit 203. The principles of the present invention are not to be limited in scope to the discussed technologies and may include other technologies with the ability to monitor corrosion.

Furthermore, as illustrated in FIG. 2, sensor 101 is housed in a protective cementitious housing 204 protecting sensor 101 from its outside elements, where cementitious housing 204 has properties that match or are similar to that of its environment. In one embodiment, housing 204 is a fiber-reinforced cementitious paste housing. Cementitious housing 204 provides physical protection to sensor 101 during construction and provides a convenient base to affix sacrificial transducer 202 (e.g., sacrificial steel washer). Polypropylene fibers may be used to reinforce the paste and control shrinkage cracking In one embodiment, the outer diameter of protective housing 204 is set at approximately 4 inches to prevent cracking during curing. In one embodiment, housing 204 has a convex shape so as to prevent trapping air below sensor 101 during the placement of concrete.

In one embodiment, diffusion layer 201 is made of material (hygroscopic) which provides a water-absorbing medium. This enables the dispersion of chloride ions (from deicing salts or salt water) in the regions of high concentrations (e.g., near cracks (localized)) to the rest of the sacrificial transducer 202 (e.g., anode of the transducer). Additionally, diffusion layer 201 ensures a more uniform distribution of corrosive salts over the entire surface of sacrificial transducer 202. This provides a uniform corrosion response mitigating the effects of localized corrosion. Diffusion layer 201 can also be used to smooth out each stage in a multi-threshold sensor improving its dynamic range and making concurrent multi-threshold detection feasible. In addition, diffusion layer 201 does not affect sensor's 101 cementitious packaging 204 (matched with the environment). Thus, the "linearity," robustness and reliability of the embedded corrosion sensor 101 is substantially improved.

The innovative design of sensor 101 enables the utilization of corrosion transducers 202 fabricated from a variety of materials and morphologies. However, the selection of a suitable sacrificial corroding element 202 is critical to the successful development of an embeddable corrosion sensor 101. To this end, sacrificial element 202 should possess the following three attributes:

1. Sacrificial element 202 should exhibit electrochemical properties that are similar to the low-carbon steels used for the manufacturing of deformed reinforcement. As a result, shifts in the response of the NC sensors 101 embedded in concrete 102 will be indicative of real active corrosion in the adjacent steel.

2. Sacrificial element 202 should be able to electromagnetically (inductive/capacitive) interact with resonator 203 (e.g., a capacitive transducer may not shield fields between reader 103 and the sensor coils but changes the resonator's capacitance).

3. Sacrificial element 202 should be inexpensive, commercially available, and mass-produced. This will minimize the final cost of NC sensor 101 and allow for the deployment of corrosion sensor 101 in typical concrete bridges.

Examples of sacrificial transducers 202 that meet these attributes include steel washers and closed wire spirals. In one embodiment, the shape of sacrificial transducers 202 corresponds to a circular, elliptical or polygon shape.

Currently designed corrosion monitored sensors that are embedded in concrete structures to monitor the corrosion of steel reinforcement can be affected by localized corrosion. The transition from uncorroded to corroded states can be halted temporarily before reaching the fully corroded state. This behavior can be the result of the formation of a dense layer of corrosion products in the crack region that subsequently block the supply of chloride ions to the active anode of the transducer and halt the corrosion process. The slower corrosion rate can also be the result of a local and unique electrochemical condition that led to the repassivation of the steel near the cracked region. As a result of adding diffusion layer 201 that is placed over transducer 202, a more uniform distribution of chloride ions over the surface of sacrificial transducer 202 mitigating the localized corrosion is ensured. Furthermore, such a design is less susceptible to false positives.

In summary, sensor 101 mitigates the undesirable effects of localized corrosion which makes the sensor response unpredictable. It is insensitive to localized corrosion effects due to the random location and size of cracks. Furthermore, the accuracy and reliability in indicating a corroded state is improved. In addition, the uniform corrosion leads to a more analog response between the sensor states. This can be particularly useful for multi-threshold detection. It benefits from all the advantages of wire-free transducer interaction which protects sensor circuitry by maintaining hermeticity. Overall, sensor 101 has improved "linearity," robustness, reliability and can reduce incidence of false negative detection events.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A corrosion detection sensor embedded within a concrete structure, comprising:
 a hermetically sealed resonant circuit comprising an inductor, a resistor and a capacitor;
 a sacrificial transducer that is inductively or capacitively coupled to said resonant circuit, wherein said sacrificial transducer is exposed to an environment outside said sensor to monitor corrosion of steel reinforcement in said concrete structure;
 a protective cementitious housing surrounding said resonant circuit and said sacrificial transducer; and
 a diffusion layer placed over said sacrificial transducer, wherein said diffusion layer enables a dispersion of a chemical species over said sacrificial transducer.

2. The corrosion detection sensor as recited in claim 1, wherein said chemical species comprises chloride ions.

3. The corrosion detection sensor as recited in claim 1, wherein said diffusion layer enables dispersion of said chemical species in regions with a higher concentration of said chemical species in comparison to regions with a lower concentration of said chemical species.

4. The corrosion detection sensor as recited in claim 3, wherein said regions with said higher concentration of said chemical species are regions of cracks in said concrete structure.

5. The corrosion detection sensor as recited in claim 1, wherein said diffusion layer distributes corrosive salts over an entire surface of said sacrificial transducer.

6. The corrosion detection sensor as recited in claim 1, wherein said diffusion layer is hygroscopic.

7. The corrosion detection sensor as recited in claim 1, wherein said diffusion layer is hydrophobic.

8. The corrosion detection sensor as recited in claim 1, wherein said diffusion layer is semi-permeable.

9. The corrosion detection sensor as recited in claim 1, wherein said sensor is interrogated through an external reader by using magnetic coupling between a coil of said reader and said resonant circuit.

10. The corrosion detection sensor as recited in claim 1, wherein said sacrificial transducer interacts wire-free with said resonant circuit.

11. The corrosion detection sensor as recited in claim 1, wherein said sacrificial transducer comprises a steel washer or a closed wire spiral.

12. The corrosion detection sensor as recited in claim 1, wherein a shape of said sacrificial transducer corresponds to one of the following: circular, elliptical and polygon.

13. An electronic structural surveillance system, comprising:
   a corrosion detection sensor embedded within a concrete structure, wherein said sensor comprises:
      a hermetically sealed resonant circuit comprising an inductor, a resistor and a capacitor;
      a sacrificial transducer that is inductively or capacitively coupled to said resonant circuit, wherein said sacrificial transducer is exposed to an environment outside said sensor to monitor corrosion of steel reinforcement in said concrete structure;
      a protective cementitious housing surrounding said resonant circuit and said sacrificial transducer; and
      a diffusion layer placed over said sacrificial transducer, wherein said diffusion layer enables a dispersion of a chemical species over said sacrificial transducer; and
   an external reader configured to interrogate said sensor by using magnetic coupling between a coil of said reader and said resonant circuit.

14. The surveillance system as recited in claim 13, wherein said chemical species comprises chloride ions.

15. The surveillance system as recited in claim 13, wherein said diffusion layer enables dispersion of said chemical species in regions with a higher concentration of said chemical species in comparison to regions with a lower concentration of said chemical species.

16. The surveillance system as recited in claim 15, wherein said regions with said higher concentration of said chemical species are regions of cracks in said concrete structure.

17. The surveillance system as recited in claim 13, wherein said diffusion layer distributes corrosive salts over an entire surface of said sacrificial transducer.

18. The surveillance system as recited in claim 13, wherein said diffusion layer is hygroscopic.

19. The surveillance system as recited in claim 13, wherein said diffusion layer is hydrophobic.

20. The surveillance system as recited in claim 13, wherein said diffusion layer is semi-permeable.

21. The surveillance system as recited in claim 13, wherein said sacrificial transducer interacts wire-free with said resonant circuit.

22. The surveillance system as recited in claim 13, wherein said sacrificial transducer comprises a steel washer or a closed wire spiral.

23. The surveillance system as recited in claim 13, wherein a shape of said sacrificial transducer corresponds to one of the following: circular, elliptical and polygon.

24. A corrosion detection sensor embedded within a concrete structure, comprising:
   a hermetically sealed resonant circuit comprising an inductor, a resistor and a capacitor;
   a plurality of sacrificial transducers that are inductively or capacitively coupled to said resonant circuit, wherein said plurality of sacrificial transducers are exposed to an environment outside said sensor to monitor corrosion of steel reinforcement in said concrete structure;
   a protective cementitious housing surrounding said resonant circuit and said plurality of sacrificial transducers; and
   one or more diffusion layers placed over one or more of said plurality of sacrificial transducers, wherein said one or more diffusion layers enable a dispersion of a chemical species over said one or more of said plurality of sacrificial transducers.

25. A corrosion detection sensor embedded within a concrete structure, comprising:
   a hermetically sealed RFID tag;
   a sacrificial transducer that is inductively or capacitively coupled to said RFID tag, wherein said sacrificial transducer is exposed to an environment outside said sensor to monitor corrosion of steel reinforcement in said concrete structure;
   a protective cementitious housing surrounding said RFID tag and said sacrificial transducer; and
   a diffusion layer placed over said sacrificial transducer, wherein said diffusion layer enables a dispersion of a chemical species over said sacrificial transducer.

* * * * *

UNITED STATES PATENT AND TRADEMARK OFFICE
CERTIFICATE OF CORRECTION

PATENT NO. : 9,581,559 B2
APPLICATION NO. : 14/459474
DATED : February 28, 2017
INVENTOR(S) : Dean P. Neikirk et al.

Page 1 of 1

It is certified that error appears in the above-identified patent and that said Letters Patent is hereby corrected as shown below:

In the Specification

Column 1, Lines 19-22, Please replace with the following:
This invention was made with government support under Grant No. 70NANB9H9011 awarded by the National Institute of Standards and Technology (NIST). The government has certain rights in the invention.

Signed and Sealed this
Twenty-second Day of August, 2023

Katherine Kelly Vidal
*Director of the United States Patent and Trademark Office*